United States Patent
Li et al.

(10) Patent No.: US 8,810,788 B2
(45) Date of Patent: Aug. 19, 2014

(54) BROAD BAND STRUCTURES FOR SURFACE ENHANCED RAMAN SPECTROSCOPY

(75) Inventors: Zhiyong Li, Redwood City, CA (US); Min Hu, Sunnyvale, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 450 days.

(21) Appl. No.: 13/254,897

(22) PCT Filed: Mar. 13, 2009

(86) PCT No.: PCT/US2009/037167
§ 371 (c)(1), (2), (4) Date: Sep. 6, 2011

(87) PCT Pub. No.: WO2010/104520
PCT Pub. Date: Sep. 16, 2010

(65) Prior Publication Data
US 2011/0317160 A1    Dec. 29, 2011

(51) Int. Cl.
*G01J 3/44* (2006.01)
*G01N 21/65* (2006.01)
*G01N 21/55* (2014.01)

(52) U.S. Cl.
CPC ............ *G01N 21/658* (2013.01); *G01N 21/553* (2013.01); *G01N 21/554* (2013.01)
USPC ....................................... 356/301

(58) Field of Classification Search
CPC .. G01N 21/658; G01N 21/553; G01N 21/554
USPC ....................................... 356/301
See application file for complete search history.

(56) References Cited

U.S. PATENT DOCUMENTS

| | | | |
|---|---|---|---|
| 5,609,907 | A | 3/1997 | Natan |
| 6,025,202 | A | 2/2000 | Natan |
| 7,288,419 | B2 | 10/2007 | Naya |
| 7,351,588 | B2 | 4/2008 | Poponin |
| 7,453,565 | B2 | 11/2008 | Wang et al. |
| 2003/0059820 | A1 | 3/2003 | Vo-Dinh |
| 2004/0265490 | A1 | 12/2004 | Yang et al. |

(Continued)

FOREIGN PATENT DOCUMENTS

| | | |
|---|---|---|
| CN | 1875490 | 12/2006 |
| CN | 101057132 | 10/2007 |

(Continued)

OTHER PUBLICATIONS

EP Supplementary European Search Report, EPO (Munich), Application No. 09841631.6, Oct. 19, 2012.

(Continued)

*Primary Examiner* — Tarifur Chowdhury
*Assistant Examiner* — Sunghee Y Gray

(57) ABSTRACT

Broad band structures for surface enhanced Raman spectroscopy are disclosed herein. Each embodiment of the structure is made up of a metal layer, and a dielectric layer established on at least a portion of the metal layer. The dielectric layer has a controlled thickness that varies from at least one portion of the dielectric layer to at least another portion of the dielectric layer. Nanostructures are established on the dielectric layer at least at the portion and the other portion, the nanostructures thus being configured to exhibit variable plasmon resonances.

15 Claims, 4 Drawing Sheets

(56) References Cited

U.S. PATENT DOCUMENTS

| | | |
|---|---|---|
| 2005/0211566 A1 | 9/2005 | Tomita et al. |
| 2006/0250924 A1 | 11/2006 | Kahle |
| 2007/0252982 A1 | 11/2007 | Wang et al. |
| 2007/0257396 A1 | 11/2007 | Wang et al. |
| 2008/0198376 A1 | 8/2008 | Poponin |
| 2010/0085566 A1* | 4/2010 | Cunningham ............... 356/301 |
| 2011/0249546 A1* | 10/2011 | Choo et al. ............... 369/112.18 |

FOREIGN PATENT DOCUMENTS

| | | |
|---|---|---|
| EP | 1580305 | 9/2005 |
| GB | 2418017 | 3/2006 |
| GB | 2419940 | 5/2006 |
| JP | 2006349463 | 12/2006 |
| JP | 2008-164584 | 7/2008 |
| JP | 2009-031023 | 2/2009 |
| WO | WO-9810289 | 3/1998 |

OTHER PUBLICATIONS

Guo, L. Jay. "Nanoimprint lithography: methods and material requirements." Advanced Materials vol. 19, No. 4, (2007), pp. 495-513.

Rueda, A. et al.,"Optical resonances of gold nanoparticles on a gold surface: quantitative correlation of geometry and resonance wavelength", New Journal of Physics, Inst. of Physics, vol. 10, No. 11, 22 pages, Nov. 1, 2008.

Mock, et al. "Distance-Dependent Plasmon Resonant Coupling Between a Gold Nanoparticle and Gold Film", Nano Letters, vol. 8, No. 8 (2008), pp. 2245-2252.

* cited by examiner

BROAD BAND STRUCTURES FOR SURFACE ENHANCED RAMAN SPECTROSCOPY

STATEMENT OF GOVERNMENT INTEREST

This invention has been made with Government support under Contract No. HR0011-09-3-0002, awarded by the Defense Advanced Research Projects Agency. The government has certain rights in the invention.

BACKGROUND

The present disclosure relates generally to broad band structures for surface enhanced Raman spectroscopy.

Raman spectroscopy is used to study the transitions between molecular energy states when monochromatic light interacts with molecules, which results in the energy of the light photons being shifted, or scattered. The energy shift provides information of the vibrational energy spacing in the molecular system. Surface enhanced Raman spectroscopy (SERS) enhances Raman scattering via molecules adsorbed on, for example, rough metal surfaces or metal nanoparticle aggregates. The Raman signal enhancement is typically related to the large electric fields generated near the metal surface due to localized surface plasmon resonance. However, the SERS signals strongly depend on the excitation light wavelength. To achieve a large Raman enhancement factor, the excitation light wavelength may be tuned in close proximity to the surface plasmon resonance of the metal nanoparticles.

BRIEF DESCRIPTION OF THE DRAWINGS

Features and advantages of embodiments of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Embodiments of the SERS structures disclosed herein enable systematic control of the plasmonic resonance of metal nanostructures over a broad electromagnetic spectrum (e.g., from near ultraviolet (UV) to near infrared (IR)). The variable plasmon resonances provide uniform SERS enhancement at many excitation wavelengths with a single device. As such, the structure(s) disclosed herein provide an advantage over structures including a single type of plasmonic resonance nanostructure, which tend to strongly depend upon the excitation wavelength used. Furthermore, it is believed that the broad band response of the SERS structures disclosed herein advantageously eliminates inefficient Raman responses at some wavelengths.

Figure 1:
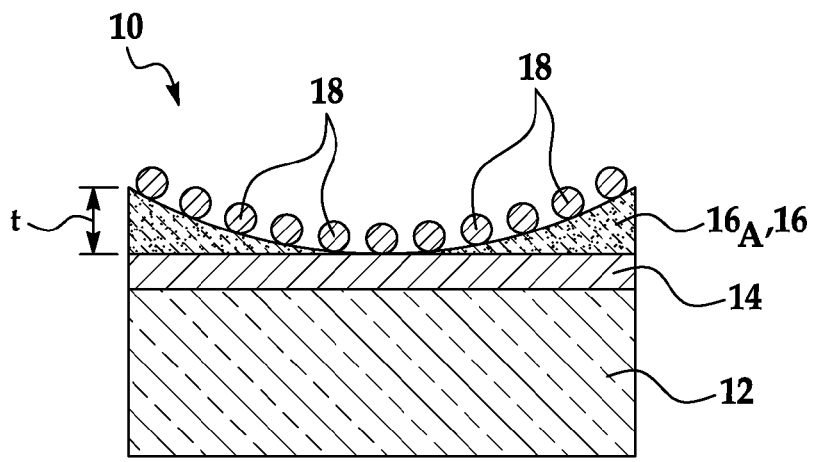
FIG. 1 is a schematic cross-sectional view of an embodiment of a broad band SERS structure having an arc shaped dielectric layer.
Figure 2:
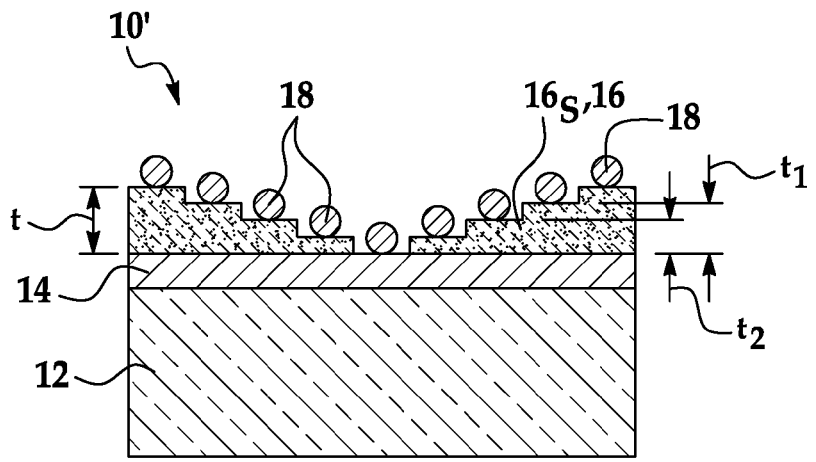
FIG. 2 is a schematic cross-sectional view of another embodiment of a broad band SERS structure having a step shaped dielectric layer.
Figure 3:
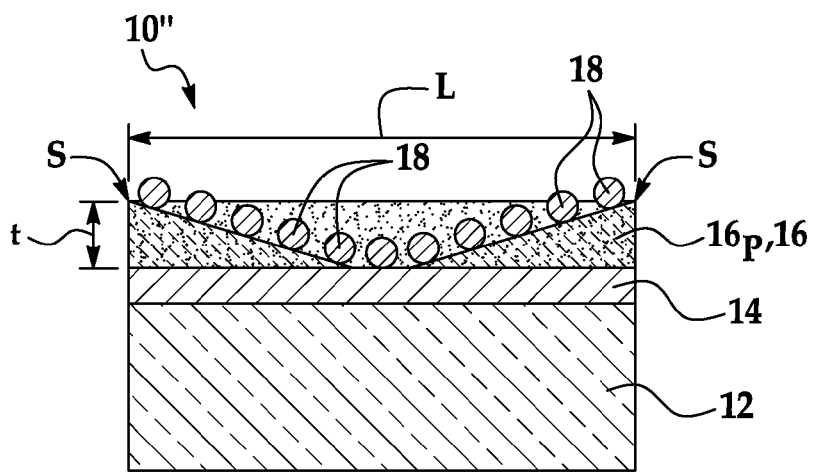
FIG. 3 is a schematic cross-sectional view of still another embodiment of a broad band SERS structure having a pyramid shaped dielectric layer.

Referring now to FIGS. 1, 2 and 3 together, various embodiments of the broad band structure 10, 10', 10" are respectively shown. Each of the structures 10, 10', 10" includes a substrate 12 having a metal layer 14 established thereon. The substrate 12 is generally formed of any suitable material. In one embodiment, the substrate 12 is made of a dielectric material. Non-limiting examples of suitable substrate materials include insulators (e.g., glass, quartz, ceramic (e.g., alumina), etc.), polymeric material(s) (e.g., polycarbonates, polyamides, acrylics, etc.), or semiconductors (e.g., silicon, InP, GaAs, InAs, $In_xGa_{1-x}As_yP_{1-y}$ (where $0<x<1$, $0<y<1$)), silicon-on-insulator (SOI) substrates, or group III-V semiconductors on silicon on SOI substrates.

The metal layer 14 is generally selected from gold, silver, copper, aluminum, or various alloys and mixtures thereof. It is believed that gold may be particularly advantageous for enhancing the stability of the structure 10, 10', 10". The metal layer 14 may be deposited via any suitable method, including chemical vapor deposition (CVD), physical vapor deposition (PVD), atomic layer deposition (ALD), plating, or the like. The metal layer 14 may have any desirable thickness. In one embodiment, the thickness ranges from about 50 nm to about 100 nm. It may be desirable that the thickness be several tens of nanometers.

Each of the structures 10, 10', 10" also includes a dielectric material 16, which, during fabrication, is patterned and cured or etched to form a dielectric layer $16_A$, $16_S$, $16_P$ having a desirable shape and a varying thickness t. The shape may be any desirable shape which results in variable spacing between the metal layer 14 and two or more of the nanostructures 18 established on the dielectric layer $16_A$, $16_S$, $16_P$. Non-limiting examples of such shapes include an arc (see FIG. 1) or semi-spherical shape, a multi-step shape (see FIG. 2), or a pyramid shape (see FIG. 3). Other suitable shapes may be utilized, such as, for example, a triangular shape in which a surface of the dielectric layer (this embodiment is not shown) has a predetermined slope relative to a surface of metal layer 14.

It is to be understood that the thickness t of the dielectric layer $16_A$, $16_S$, $16_P$ may continuously vary along an entire length L of the layer $16_A$, $16_S$, $16_P$ (as shown in FIGS. 1 and 3), or may vary from one portion to another. In the latter embodiment, one portion of the dielectric layer $16_A$, $16_S$, $16_P$ may have a consistent thickness $t_1$ across part of the length L, while another portion has a different consistent thickness $t_2$ across another part of the length L (as shown in FIG. 2). It is to be understood that in the embodiments shown in FIGS. 1 and 3, even though the thickness t varies continuously, the thickness t may be the same at certain points along the length L. For example, when the dielectric layer $16_P$ has the pyramidal shape, the opposed sides S of the pyramid have the same varying thickness t.

Suitable dielectric materials 16 for forming the dielectric layer $16_A$, $16_S$, $16_P$ include insulating materials, such as $SiO_2$, $Si_3N_4$, glass, or insulating polymers. In some embodiments, the dielectric material 16 is curable. It is to be understood that the various methods for forming the different embodiments of the dielectric layer $16_A$, $16_S$, $16_P$ will be described further hereinbelow in reference to FIGS. 4 and 5.

Nanostructures 18 are established on the dielectric layer $16_A$, $16_S$, $16_P$. Suitable deposition techniques for establishing the nanostructures 18 include a Langmuir Blodgett method or a casting method.

Due to the varying thickness t of the dielectric layer $16_A$, $16_S$, $16_P$, at least some of the deposited nanostructures 18 are positioned at different distances from the surface of the metal layer 14 in comparison with at least some other of the deposited nanostructures 18. Furthermore, at least some of the nanostructures 18 exhibit varying plasmonic resonances from at least some of the other nanostructures 18, due, at least in part to the varying distances of the respective nanostructures 18 from the metal layer 14. As such, the thickness t of the dielectric layer $16_A$, $16_S$, $16_P$ may be controlled to achieve desirable nanostructure 18 plasmonic resonance frequencies. In an embodiment, the desirable range of the varying thickness is from about 0 nm to about 2r nm, where "r" is the radius of the nanostructure 18. It is to be understood, however, that the upper end of the range may be larger than 2r or smaller than 2r, if desirable. The thickness used will depend, at least in part, on the desirable plasmonic resonances. For example, if metal nanoparticles are used having a 10 nm radius, the varying thickness of the dielectric layer 16 may range from about 0 nm to about 50 nm.

As a non-limiting example of the structure 10, 10', 10", silver nanoparticles 18 having diameters of about 40 nm are utilized, and the varying thickness of the dielectric layer 16 ranges from about 0 nm to about 40 nm or more. The corresponding plasmon frequencies in this non-limiting example are as follows: at 0 nm dielectric layer 16 thickness, the plasmon resonance of the particle(s) 18 ranges from 700 nm to 800 nm; at 10 nm dielectric layer 16 thickness, the plasmon resonance of the particle(s) 18 ranges from 500 nm to 600 nm; at 20 nm dielectric layer 16 thickness, the plasmon resonance of the particle(s) 18 is about 500 nm; and at a dielectric layer 16 thickness of 30 nm or more, the plasmon resonance of the particle(s) 18 ranges from 400 nm to 500 nm. Another non-limiting example of the structures 10, 10', 10" includes gold spherical nanoparticles 18 having diameters of 10 nm, and a silicon dioxide dielectric layer 16 with the varying thickness ranging from 0 nm to 100 nm.

As mentioned in the previous non-limiting examples, silver and gold are suitable materials for the nanostructures 18. Other non-limiting examples of suitable nanostructure materials are copper, aluminum, or alloys of any of the listed metals. The nanostructures 18 may be particles or have some other desirable configuration. Furthermore, the nanostructures 18 may have any desirable shape including spheres, cubes, polyhedral shapes, arbitrary shapes, or the like, as long as at least one dimension (e.g., the diameter in the case of particles) of the nanostructures 18 is on the nanoscale (i.e., ranging from about 1 nm to about 300 nm).

The structures 10, 10', 10" disclosed herein are suitable for use in standard Raman detection procedures. Generally, analyte molecules are distributed on the SERS structure 10, 10', 10" (i.e., over the nanostructures 18) and are subsequently subjected to laser excitation of suitable wavelengths. The resulting signals are detected using known detectors.

Figure 4A:
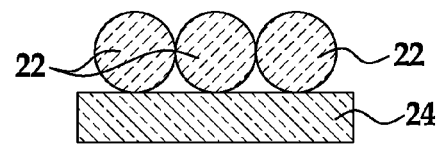
FIGS. 4A through 4G are schematic cross-sectional views which together illustrate an embodiment of a method for forming an embodiment of the broad band SERS structure having the arc shaped dielectric layer.
Figure 4B:
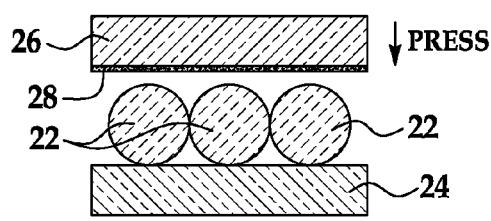
Figure 4C:
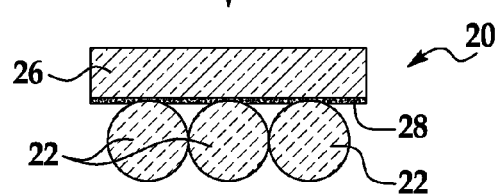
Figure 4D:
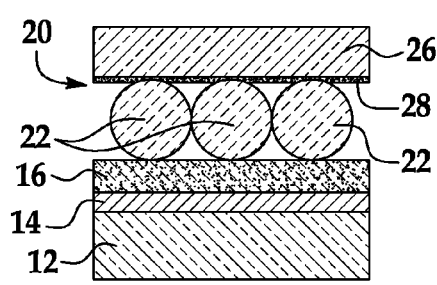
Figure 4G:
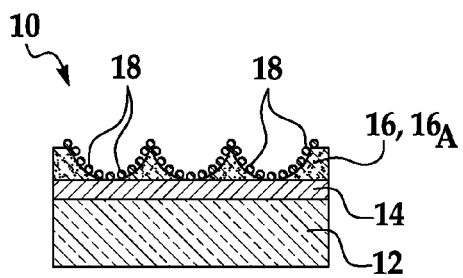

Referring now to FIGS. 4A through 4G, an embodiment of the method for forming the structure 10 (different embodiments of which are shown in FIGS. 1 and 4G) is depicted. More specifically, FIGS. 4A through 4C illustrate the formation of an imprint mold 20, and FIGS. 4D through 4G illustrate the formation of the structure 10 using the imprint mold 20.

As shown in FIG. 4A, a plurality of spherical beads 22 are established on a substantially flat surface of a substrate 24. The substrate 24 may be any suitable material, such as silicon, glass, quartz, or any of the other materials listed for substrate 12. In one embodiment, the phrase "substantially flat", when used to describe the substrate 24 surface, means that the surface is planar and has a slope of zero. The substantially flat surface may, in some instances, have minor surface irregularities that do not interfere with the desirable layout of the spherical beads 22 thereon.

The spherical beads 22 are selected to have a predetermined size (e.g., diameter). It is to be understood that the size dictates the arc shape that is formed in the dielectric material 16. In a non-limiting example, the diameter of the spherical beads 22 ranges from about 50 nm to about 5 μm. In an embodiment, the spherical beads 22 are selected from polymeric or glass beads.

As shown in FIG. 4A, the beads 22 are established on the substrate 24 such that they are close together in a relatively uniform manner. Establishing the beads 22 on the substrate 24 may be accomplished by first suspending the beads 22 in a suitable fluid (e.g., water or a suitable non-dissolving organic solvent), and then depositing (e.g., via casting, spin-coating, etc.) the suspension on the substrate 24. The fluid is then evaporated, and the beads 22 remain closely packed on the substrate 24.

Another substantially flat substrate 26, having a thin layer of adhesive material 28 thereon, is then pressed into the substrate 24 such that the adhesive material 28 contacts the beads 22. This is shown in FIG. 4B. It is to be understood that any of the previously listed substrate materials are suitable for substrate 24, and that any desirable adhesive material 28 may be used. As non-limiting examples, an epoxy or a curable glue may be a suitable adhesive material 28. The thickness of the adhesive material 28 is substantial enough to adhere the beads 22 to the substrate 26 without flowing around the beads 22 or between adjacent beads 22. Generally, the thickness of the adhesive material 28 is smaller than the radius of the beads 22 used.

The adhesive material 28, which is in contact with the beads 22, is then cured to anchor the beads 22 to the substrate 26. The curing temperature will depend upon the adhesive material 28 selected, and is low enough to not deleteriously affect the beads 22. This forms the imprint mold 20, as shown in FIG. 4C.

Figure 4F:
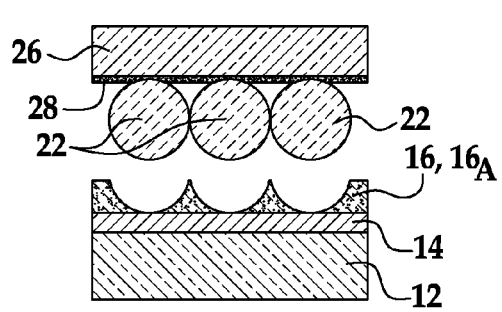
Figure 4E:
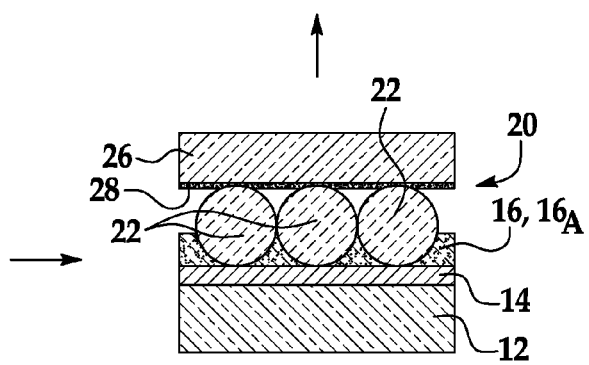

As shown in FIGS. 4D and 4E, the imprint mold 20 is used to pattern the dielectric material 16. The dielectric material 16 is established on the metal layer 14, which is established on the substrate 12. Materials for, thicknesses of, and methods for depositing such layer 14 and material 16 are described hereinabove in reference to FIGS. 1-3.

At this point, the dielectric material 16 is a curable dielectric which has not yet been cured, and thus is readily conformable to the pattern defined by the beads 22 when the imprint mold 20 is pressed therein (see, e.g., FIG. 4E). It is to be understood that the imprint mold 20 may be pressed into and/or through all or a portion of the depth of the dielectric material 16. The depth into and/or through which the imprint mold 20 is pressed will depend upon the desired variable thickness t for the resulting dielectric layer $16_A$. For example, if it is desirable that the variable thickness t dielectric layer $16_A$ be as thin as possible, the mold 20 may be pressed through the entire depth of the dielectric material 16.

While the imprint mold 20 is pressed to a desirable depth in the dielectric material 16, the material 16 is cured. Curing may be accomplished at a temperature suitable for the material 16 selected, and may be accomplished via thermal curing or UV curing. The pattern of the beads 22 is therefore transferred to the resulting dielectric layer $16_A$. The mold 20 is then released, as shown in FIG. 4F. The nanostructures 18 are deposited on the patterned dielectric layer $16_A$ via one of the methods described hereinabove. The resulting structure 10 is shown in FIG. 4G. It is to be understood that the spherical bead imprint mold 20 may be used to form an arc shape or a semi-spherical shape. The resulting pattern in the dielectric layer depends, at least in part, on the width of the dielectric material 16 (not shown in FIG. 4G, but would be extending into the paper), and the diameter of the beads 22 used.

Referring now to FIGS. 5A through 5F, another embodiment of the method for forming the structure 10 is depicted. While the dielectric layer $16_A$ is shown being formed in this embodiment, it is to be understood that the other patterned dielectric layers $16_S$, $16_P$ may be formed via this method.

Figure 5A:
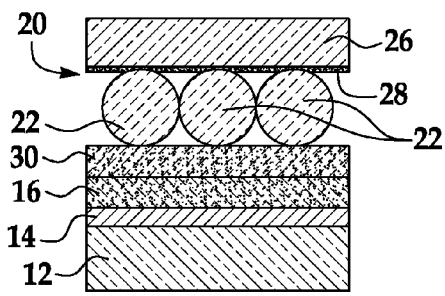
FIGS. 5A through 5F are schematic cross-sectional views which together illustrate another embodiment of a method for forming an embodiment of the broad band SERS structure.

As shown in FIG. 5A, the imprint mold 20 is utilized. However, rather than pressing the imprint mold 20 directly into the dielectric material 16 which ultimately forms the dielectric layer $16_A$, the imprint mold 20 is pressed into a resist layer 30 that is established on the dielectric material 16. In this embodiment, the resist layer 30 is a curable polymer, such that it conforms to and may be set to the pattern of the imprint mold 20. Also in this embodiment, the dielectric material 16 may not be a curable dielectric material. This embodiment of the method increases the list of dielectric materials 16 that may be used to form the dielectric layer $16_A$. As such, in this embodiment, the list of suitable material is not limited to curable dielectric materials.

Figure 5B:
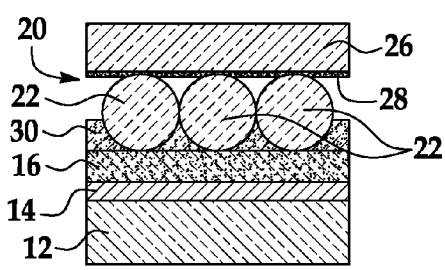
Figure 5F:
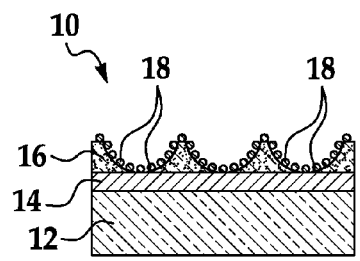
Figure 5E:
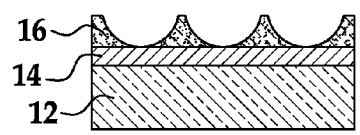
Figure 5C:
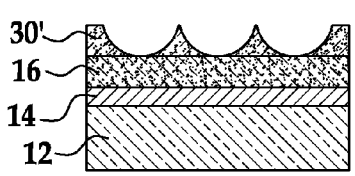
Figure 5D:
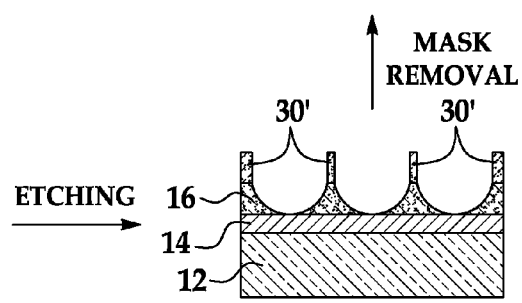

As shown in FIG. 5B, the imprint mold 20 is used to transfer the pattern to the resist layer 30. After the imprinting and curing processes are complete, a resist mask 30' is formed, as shown in FIG. 5C. The cured resist layer having the pattern formed therein is a sacrificial etching mask 30' that is used to pattern the underlying dielectric material 16 in a subsequent etching process. In an embodiment, directional etching (such as reactive ion etching) may be used to further transfer the pattern into the dielectric material 16 (see FIG. 5D). As shown, the underlying dielectric material 16 is patterned to form the dielectric layer $16_A$. Such an etching process may be utilized as long as the proper etching conditions may be selected. The residual resist mask 30', if any, is then removed via a suitable solve or another etchant.

The nanostructures 18 are deposited on the patterned dielectric layer $16_A$ via one of the methods described hereinabove. The resulting structure 10 is shown in FIG. 5F.

Figure 6:
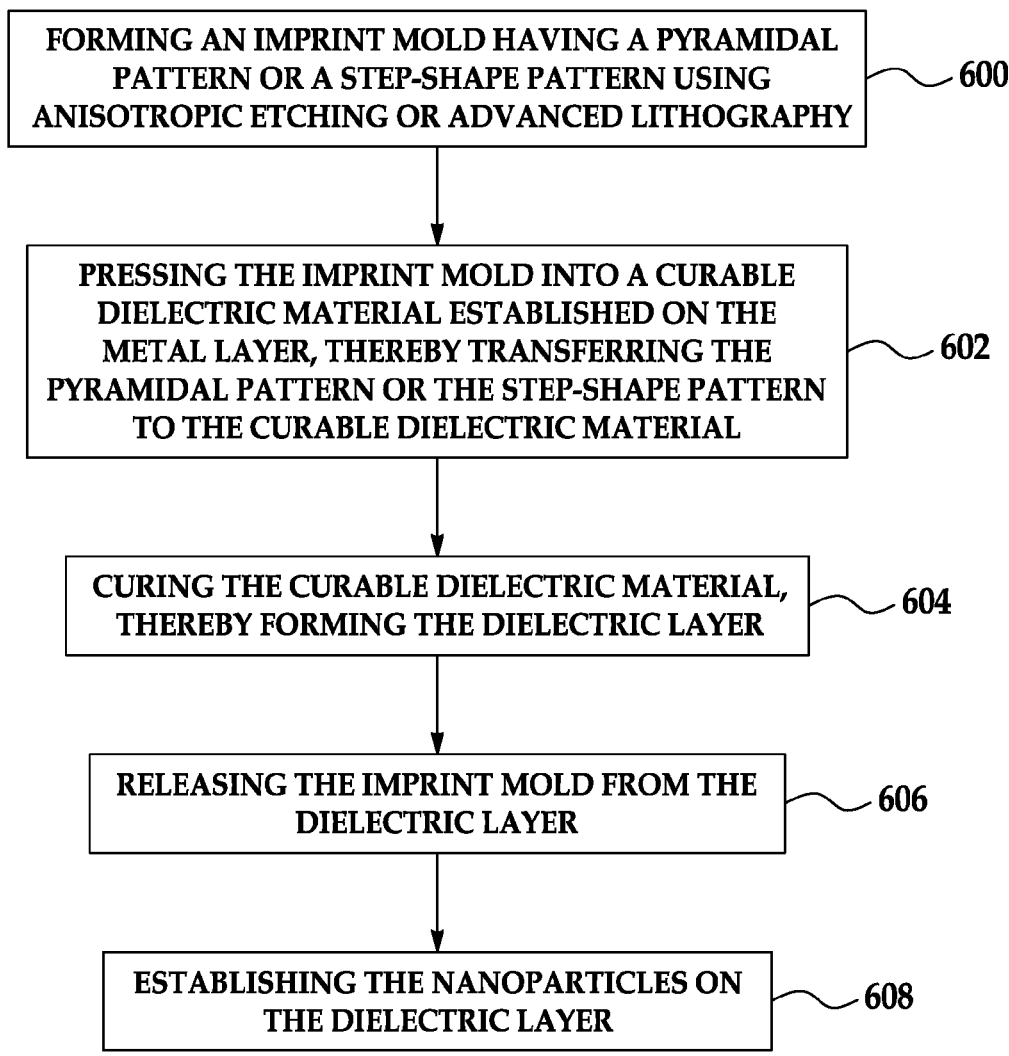
FIG. 6 is a flow diagram depicting an embodiment of a method for forming an embodiment of the broad band SERS structure having either the pyramid shaped dielectric layer or the step shaped dielectric layer.

Referring now to FIG. 6, an embodiment of the method for forming the structure 10' or 10" (embodiments of which are shown in FIGS. 2 and 3, respectively) is depicted. As shown at reference numeral 600, the method includes forming an imprint mold.

When it is desirable to form the structure 10', the imprint mold includes a step shaped pattern. It is to be understood that the inverse of this imprint mold pattern is ultimately transferred to the dielectric material 16. This step shaped pattern may include any desirable number of steps, as long as at least one step has a thickness that is different from one other step. In this particular embodiment, an advanced lithography technique (e.g., focused ion beam (FIB) lithography, electron beam (e-beam) lithography) may be used to generate the desirable pattern in a suitable mold material. Suitable mold materials include, but are not limited to quartz, silicon, silicon nitride, glass, diamond-like material, etc.

It is to be understood that advanced lithography techniques may also be used to generate an imprint mold having another desirable shape, such as a triangular shape with a single slanted surface.

When it is desirable to form the structure 10", the imprint mold includes a pyramidal pattern. Such a pyramid pattern may be formed in a crystalline silicon substrate via anisotropic etching (e.g., a wet etching process). A square pattern is initially wet etched into the surface of the crystalline silicon substrate. As the etching process continues through a depth of the crystalline silicon substrate, the initially square pattern decreases until the pyramidal pattern is formed therein. For example, wet etching is selective toward the <100> surface of the crystalline silicon substrate, thereby enabling the square pattern to initially be formed therein. However, as etching continues, a <111> surface is reached, which slows down the etching and causes the pyramid shape (which is actually an inverted pyramid) to form.

The pyramid shape formed in the crystalline silicon substrate may be transferred to a mold material (e.g., a curable resist) by depositing the mold material on at least the etched portion of the crystalline silicon substrate. The mold material is then cured, which sets the pyramidal pattern into the mold material and forms the imprint mold.

As shown at reference numeral 602, after the desirable imprint mold is formed, it is pressed into the curable dielectric material 16 (which, as described above, is established on the metal layer 14 and the substrate 12). By pressing the mold into the material 16, the inverse of the step shape pattern or the pyramidal pattern is transferred to the dielectric material 16. This material is then cured to form the dielectric layer $16_S$, $16_P$, as shown at reference numeral 604. The imprint mold is then released (see reference numeral 606), and the nanostructures 18 are established on exposed surfaces of the dielectric layer $16_S$, $16_P$ (see reference numeral 608) using techniques previously described herein.

While several embodiments have been described in detail, it will be apparent to those skilled in the art that the disclosed embodiments may be modified. Therefore, the foregoing description is to be considered exemplary rather than limiting.

What is claimed is:

1. A broad band structure for surface enhanced Raman spectroscopy, comprising:
   a metal layer;
   a dielectric layer established on at least a portion of the metal layer, the dielectric layer having a controlled thickness that varies from at least one portion of the dielectric layer to at least an other portion of the dielectric layer; and
   nanostructures established on the dielectric layer at least at the portion and the other portion, the nanostructures thus being configured to exhibit variable plasmon resonances.

2. The broad band structure as defined in claim 1 wherein the dielectric layer has an arc shape.

3. The broad band structure as defined in claim 1 wherein at least a portion of a surface of the dielectric layer has a slope relative to a surface of the metal layer.

4. The broad band structure as defined in claim 1 wherein the dielectric layer has a pyramid shape.

5. The broad band structure as defined in claim 1 wherein the thickness of the dielectric layer is continuously varied along an entire length of the dielectric layer.

6. The broad band structure as defined in claim 1 wherein the dielectric layer has a multi-step shape in which the portion and the other portion each define a step in the multi-step shape.

7. A method for making the broad band structure as defined in claim 1, the method comprising:

assembling a plurality of spherical beads having a predetermined size onto a first substrate;

anchoring the plurality of spherical beads to a second substrate via an adhesive established on a surface of the second substrate, thereby forming an imprint mold;

pressing the imprint mold into a curable dielectric material established on the metal layer, thereby transferring a pattern of the plurality of spherical beads to the curable dielectric material;

curing the curable dielectric material, thereby forming the dielectric layer;

releasing the imprint mold from the dielectric layer; and establishing the nanostructures on the dielectric layer.

8. The method as defined in claim 7, further comprising controlling the varying thickness of the dielectric layer by selecting the predetermined size of the plurality of spherical beads.

9. The method as defined in claim 7 wherein the assembling of the plurality of spherical beads onto the first substrate is accomplished by:

depositing a suspension including the plurality of spherical beads therein onto a surface of the first substrate; and evaporating a liquid from the suspension;

and wherein the anchoring of the plurality of spherical beads to the second substrate is accomplished by:

contacting the plurality of spherical beads with the adhesive established on the surface of the second substrate; and curing the adhesive, thereby securing the plurality of spherical beads to the cured adhesive.

10. The method as defined in claim 7 wherein the establishing of the nanostructures on the dielectric layer is accomplished via a Langmuir-Blodgett method or a casting method.

11. A method for making the broad band structure as defined in claim 1, the method comprising:

pressing an imprint mold having a pattern into a curable resist layer established on a dielectric material which is established on the metal layer, thereby transferring the pattern to the curable resist layer;

curing the curable resist layer, thereby forming an etching mask;

releasing the imprint mold from the etching mask;

etching the dielectric material so as to transfer the pattern of the etching mask to the dielectric material and form the dielectric layer;

removing the etching mask; and establishing the nanostructures on the dielectric layer.

12. A method for making the broad band structure as defined in claim 1, the method comprising:

forming an imprint mold having a pyramidal pattern or a step-shape pattern using anisotropic etching or advanced lithography;

pressing the imprint mold into a curable dielectric material established on the metal layer, thereby transferring the pyramidal pattern or the step-shape pattern to the curable dielectric material;

curing the curable dielectric material, thereby forming the dielectric layer;

releasing the imprint mold from the dielectric layer; and establishing the nanostructures on the dielectric layer.

13. The method as defined in claim 12 wherein forming the imprint mold having the pyramidal pattern using anisotropic etching is accomplished by:

wet etching an initially square pattern into a surface of a crystalline silicon substrate;

continuing wet etching through a depth of the crystalline silicon substrate, whereby the initially square pattern decreases through the depth until an inverse of the pyramidal pattern is formed in the crystalline silicon substrate;

depositing a resist material on the crystalline silicon substrate such that the pyramidal pattern transfers to the resist; and curing the resist material, thereby forming the imprint mold.

14. The method as defined in claim 12 wherein forming the imprint mold having the step-shape pattern using advanced lithography is accomplished using focused ion beam lithography or electron beam lithography in conjunction with an etching process.

15. The method as defined in claim 14, further comprising defining at least one step in the step-shape pattern to have a different thickness than at least one other step in the step-shape pattern.

* * * * *